United States Patent [19]

Wessling-Resnick et al.

[11] Patent Number: 5,780,264

[45] Date of Patent: Jul. 14, 1998

[54] IRON TRANSPORT PROTEIN

[75] Inventors: Marianne Wessling-Resnick. Boxborough. Mass.; Jesus Gutierrez. Greenfield. Ind.

[73] Assignee: The President and Fellows of Harvard College. Cambridge. Mass.

[21] Appl. No.: 806,581

[22] Filed: Feb. 25, 1997

Related U.S. Application Data

[60] Provisional application Nos. 60/019,528, Jun. 6, 1996, and 60/056,915, Feb. 26, 1996.
[51] Int. Cl.$^6$ .............. C12P 21/00; C12P 19/34; C12N 15/63; C07H 21/04
[52] U.S. Cl. .............. 435/69.1; 435/91.1; 435/252.3; 435/320.1; 435/325; 536/23.5
[58] Field of Search .................. 435/69.1, 91.1, 435/252.3, 320.1, 325; 536/23.5

[56] References Cited

PUBLICATIONS

Gutierrez et al. Molecular mechanisms of iron transport. Critical Reviews in Eukaryotic Gene Expression vol. 6(1): 1–14 Feb. 1996.

*Primary Examiner*—Nancy Degen
*Assistant Examiner*—William Sandals
*Attorney, Agent, or Firm*—Hale and Dorr LLP

[57] ABSTRACT

This invention is directed to a novel protein of general significance to the cellular transport of nontransferrin bound iron. This heretofore unidentified protein, which is termed "stimulator of Fe (iron) transport" (SFT) protein, is essential to an alternative pathway of iron uptake. The cDNA encoding the SFT protein has been cloned and sequenced. The gene for the SFT protein has been mapped to chromosome 10. 17% of the distance from the centromere to the telomere of chromosome arm 10q, an area that corresponds to band 10q21. In addition, the amino acid structural identity of the SFT protein has been deduced, represented in a predicted transmembrane structure with a 6-transmembrane motif.

9 Claims, 3 Drawing Sheets

| | | | | | |
|---|---|---|---|---|---|
| 1 | GAATTCGGCT | GTCGCACTTA | CTGTTCAATA | GTATATACTC | TGTATTTGAA |
| 51 | AAATAGATGT | ATATATTCTA | GGTGATAAAT | TAAAAATGAA | AGAATTTAAT |
| 101 | CATTGGAAAG | TATTAAATAT | ATATTGCTTA | TCTTCTCCAA | GGAAGAGGAG |
| 151 | TTCTCTCGTA | CCCATCCAAA | CTGACCTAAT | TCTCAAGCTG | CTTCATCTTG |
| 201 | CTTGTACTGT | AGGTTCATTT | GCAATTTGTA | GATTATGCTC | CTTCAGGATT |
| 251 | GGCTTTTGTA | AATTTCTGTT | AGAAGCTGGT | TTCTGCATTT | TTGATTTTTG |
| 301 | TGTATTTGGA | TACATTTCA | TATTGTGCAG | AGAAATCCAT | GAGTTAAAAA |
| 351 | ATTATTTTTC | CCTGTTTAT | TTCTGCATGA | ACCTAAGTCA | CATTGACCCA |
| 401 | GTAATTGATA | TATGTGTGAT | TATTGCAATT | AAGTATAAGA | AGGTAGAATA |
| 451 | TATAGTTTTA | TTAGACAGAT | GCTTCCTGAA | ATATTATTTT | GTATGTTTTT |
| 501 | ACTATATCCT | TTTTGTGTAT | CTACAGATAC | AACAGACATG | CAAGAGAATG |
| 551 | GACTCAGAAA | TATGCAATGT | AAAAATCAAA | AACATTTTCA | TATATAACCA |
| 601 | GAGTACTGTA | AAATCTAGGT | TTTTTTTCAA | CATTAGCAGT | AAATTGAGCA |
| 651 | CTGTTTACCT | GTTTCATTGT | ACCATGAAAC | CATTTGATTT | TTACCATTTT |
| 701 | AAATGTGTCT | CAAGCAAGAC | AAAACAAACT | TCCAAAAATA | CCCTTAAGAC |
| 751 | TGTGATGAGA | GCATTTATCA | TTTTGTATGC | ATTGAGAAAG | ACATTTATTA |

FIG. 1A

```
1    GAATTCGGCT GTCGCACTTA CTGTTCAATA GTATATACTC TGTATTTGAA
51   AAATAGATGT ATATATTCTA GGTGATAAAT TAAAAATGAA AGAATTTAAT
101  CATTGGAAAG TATTAAATAT ATATTGCTTA TCTTCTCCAA GGAAGAGGAG
151  TTCTCTCGTA CCCATCCAAA CTGACCTAAT TCTCAAGCTG CTTCATCTTG
201  CTTGTACTGT AGGTTCATTT GCAATTTGTA GATTATGCTC CTTCAGGATT
251  GGCTTTTGTA AATTTCTGTT AGAAGCTGGT TTCTGCATTT TTGATTTTTG
301  TGTATTTGGA TACATTTTCA TATTGTGCAG AGAAATCCAT GAGTTAAAAA
351  ATTATTTTTC CCTGTTTTAT TTCTGCATGA ACCTAAGTCA CATTGACCCA
401  GTAATTGATA TATGTGTGAT TATTGCAATT AAGTATAAGA AGGTAGAATA
451  TATAGTTTTA TTAGACAGAT GCTTCCTGAA ATATTATTTT GTATGTTTTT
501  ACTATATCCT TTTTGTGTAT CTACAGATAC AACAGACATG CAAGAGAATG
551  GACTCAGAAA TATGCAATGT AAAAATCAAA AACATTTTCA TATATAACCA
601  GAGTACTGTA AAATCTAGGT TTTTTTTCAA CATTAGCAGT AAATTGAGCA
651  CTGTTTACCT GTTTCATTGT ACCATGAAAC CATTTGATTT TTACCATTTT
701  AAATGTGTCT CAAGCAAGAC AAAACAAACT TCCAAAAATA CCCTTAAGAC
751  TGTGATGAGA GCATTTATCA TTTTGTATGC ATTGAGAAAG ACATTTATTA
```

FIG. 1B

```
 801 TGGTTTTTAA GATACTTGGA CATCTGCATC TTCAGCTTAC AAGATCTACA
 851 ATGCAGCTGA AAAAGCAACC AAATTATTTT TTGCTGAAAA CTAGATGTTT
 901 TTTACATGAG AAAATACTGT ATGTGTGTCT AAGATGTCAG TTTTATAAAT
 951 CTGTATTCAG ATTTCATCCT TTGTTAGCTC ACTTATATAT TTGTATTTTT
1001 TTTCTGTATA GAACTAAATA TATTCTATTT ACATGTATGT CAACTCATTA
1051 CTTTTTTCCT GTGAACAGTA TTGAAAACCC CAACCGGCTG ATAATTAAGT
1101 GAATTAACTG TGTCTCCCTT GTCTTAGGAT ATTCTGTAGA TTGATTGCAG
1151 ATTTCTTAAA TCTGAAATGA CTTTACACTG TAATTCTCAG CATACTGATT
1201 ATGGAGAACA CTTGTTTTGA ATTTTGTTAT ACTTGACTTA ACTTATTGC
1251 AATGTGAATT AATTGACTGC TAAGTAGGAA GATGTGTAAC TTTTATTTGT
1301 TGCTATTCAC ATTTGAATTT TTTCCTGTAT AGGCAATATT ATATTGACAC
1351 CTTTTACAGA TCTTACTGTA GCAAAAACCA TATAAATAAA ATGCTTTTTC
1401 TGCT
```

```
  1  MKEFNHWKVL  NIYCLSSPRK  RSSLVPIQTD  LILKLLHLAC  TVGSFAICRL
 51  CSFRIGFCKF  LLEAGFCIFD  FCVFGYIFIL  CREIHELKNY  FSLFYFCMNL
101  SHIDPVIDIC  VIIAIKYKKV  EYIVLLDRCF  LKYYFVCFYY  ILFVYLQIQQ
151  TCKRMDSEIC  NVKIKNIFIY  NQSTVKSRFF  FNISSKLSTV  YLFHCTMKPF
201  DFYHFKCVSS  KTKQTSKNTL  KTVMRAFIIL  YALRKTFIMV  FKILGHLHLQ
251  LTRSTMQLKK  QPNYFLLKTR  CFLHEKILYV  CLRCQFYKSV  FRFHPLLAHF
301  ICIFFLYRT   KYILFTCMST  HYFFPVNSIE  NPNRLIIK*
```

FIG. 2

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1395 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

```
GAATTCGGCT  GTCGCACTTA  CTGTTCAATA  GTATATACTC  TGTATTTGAA  AAATAGATGT     60
ATATATTCTA  GGTGATAAAT  TAAAAATGAA  AGAATTTAAT  CATTGGAAAG  TATTAAATAT    120
ATATTGCTTA  TCTTCTCCAA  GGAAGAGGAG  TTCTCTCGTA  CCCATCCAAA  CTGACCTAAT    180
TCTCAAGCTG  CTTCATCTTG  CTTGTACTGT  AGGTTCATTT  GCAATTTGTA  GATTATGCTC    240
CTTCAGGATT  GGCTTTTGTA  AATTTCTGTT  AGAAGCTGGT  TTCTGCATTT  TTGATTTTTG    300
TGTATTTGGA  TACATTTTCA  TATTGTGCAG  AGAAATCCAT  GAGTTAAAAA  ATTATTTTC     360
CCTGTTTTAT  TTCTGCATGA  ACCTAAGTCA  CATTGACCCA  GTAATTGATA  TATGTGTGAT    420
TATTGCAATT  AAGTATAAGA  AGGTAGAATA  TATAGTTTTA  TTAGACAGAT  GCTTCCTGAA    480
ATATTATTTT  GTATGTTTTT  ACTATATCCT  TTTTGTGTAT  CTACAGATAC  AACAGACATG    540
CAAGAGAATG  GACTCAGAAA  TATGCAATGT  AAAAATCAAA  AACATTTTCA  TATATAACCA    600
GAGTACTGTA  AAATCTAGGT  TTTTTTTCAA  CATTAGCAGT  AAATTGAGCA  CTGTTTACCT    660
GTTTCATTGT  ACCATGAAAC  CATTTGATTT  TTACCATTTT  AAATGTGTCT  CAAGCAAGAC    720
AAAACAAACT  TCCAAAAATA  CCCTTAAGAC  TGTGATGAGA  GCATTTATCA  TTTTGTATGC    780
ATTGAGAAAG  ACATTTATTA  TGGTTTTTAA  GATACTTGGA  CATCTGCATC  TTCAGCTTAC    840
AAGATCTACA  ATGCAGCTGA  AAAAGCAACC  AAATTATTTT  TTGCTGAAAA  CTAGATGTTT    900
TTTACATGAG  AAAATACTGT  ATGTGTGTCT  AAGATGTCAG  TTTTATAAAT  CTGTATTCAG    960
ATTCATCCTT  TTGTTAGCTC  ACTTTATAAT  TTGTATTTTT  TTTCTGTATA  GAACTAAATA   1020
ACATGTATGT  CAACTCATTA  CTTTTTTCCT  GTGAACAGTA  TTGAAAACCC  CAACCGGCTG   1080
ATAATTAAGT  GAATTAACTG  TGTCTCCCTT  GTCTTAGGAT  ATTCTGTAGA  TTGATTGCAG   1140
ATTTCTTAAA  TCTGAAATGA  CTTTACACTG  TAATTCTCAG  CATACTGATT  ATGGAGAACA   1200
CTTGTTTTGA  ATTTTGTTAT  ACTTGACTTA  ACTTTATTGC  AATGTGAATT  AATTGACTGC   1260
TAAGTAGGAA  GATGTGTAAC  TTTTATTTGT  TGCTATTCAC  ATTTGAATTT  TTTCCTGTAT   1320
AGGCAATATT  ATATTGACAC  CTTTTACAGA  TCTTACTGTA  GCAAAAACCA  TATAAATAAA   1380
ATGCTTTTTC  TGCTA                                                        1395
```

( 2 ) INFORMATION FOR SEQ ID NO:2:

( i ) SEQUENCE CHARACTERISTICS:
        ( A ) LENGTH: 337 amino acids
        ( B ) TYPE: amino acid
        ( C ) STRANDEDNESS: single
        ( D ) TOPOLOGY: linear ( i i ) MOLECULE TYPE:

( i i i ) HYPOTHETICAL: NO ( i v ) ANTI-SENSE: NO ( x i ) SEQUENCE DESCRIPTION: SEQ ID NO:2:

| Met | Lys | Glu | Phe | Asn | His | Trp | Lys | Val | Leu | Asn | Ile | Tyr | Cys | Leu | Ser |
|---|---|---|---|---|---|---|---|---|---|---|---|---|---|---|---|
| 1 | | | | 5 | | | | | 10 | | | | | 15 | |
| Ser | Pro | Arg | Lys | Arg | Ser | Ser | Leu | Val | Pro | Ile | Gln | Thr | Asp | Leu | Ile |
| | | | 20 | | | | | 25 | | | | | 30 | | |
| Leu | Lys | Leu | Leu | His | Leu | Ala | Cys | Thr | Val | Gly | Ser | Phe | Ala | Ile | Cys |
| | | | 35 | | | | 40 | | | | | 45 | | | |
| Arg | Leu | Cys | Ser | Phe | Arg | Ile | Gly | Phe | Cys | Lys | Phe | Leu | Leu | Glu | Ala |
| | 50 | | | | | 55 | | | | | 60 | | | | |
| Gly | Phe | Cys | Ile | Phe | Asp | Phe | Cys | Val | Phe | Gly | Tyr | Ile | Phe | Ile | Leu |
| 65 | | | | | 70 | | | | | 75 | | | | | 80 |
| Cys | Arg | Glu | Ile | His | Glu | Leu | Lys | Asn | Tyr | Phe | Ser | Leu | Phe | Tyr | Phe |
| | | | | 85 | | | | | 90 | | | | | 95 | |
| Cys | Met | Asn | Leu | Ser | His | Ile | Asp | Pro | Val | Ile | Asp | Ile | Cys | Val | Ile |
| | | | 100 | | | | | 105 | | | | | 110 | | |
| Ile | Ala | Ile | Lys | Tyr | Lys | Lys | Val | Glu | Tyr | Ile | Val | Leu | Leu | Asp | Arg |
| | | | 115 | | | | | 120 | | | | | 125 | | |
| Cys | Phe | Leu | Lys | Tyr | Tyr | Phe | Val | Cys | Phe | Tyr | Tyr | Ile | Leu | Phe | Val |
| | | 130 | | | | | 135 | | | | | 140 | | | |
| Tyr | Leu | Gln | Ile | Gln | Gln | Thr | Cys | Lys | Arg | Met | Asp | Ser | Glu | Ile | Cys |
| 145 | | | | | 150 | | | | | 155 | | | | | 160 |
| Asn | Val | Lys | Ile | Lys | Asn | Ile | Phe | Ile | Tyr | Asn | Gln | Ser | Thr | Val | Lys |
| | | | | 165 | | | | | 170 | | | | | 175 | |
| Ser | Arg | Phe | Phe | Phe | Asn | Ile | Ser | Ser | Lys | Leu | Ser | Thr | Val | Tyr | Leu |
| | | | 180 | | | | | 185 | | | | | 190 | | |
| Phe | Gly | Cys | Thr | Met | Lys | Pro | Phe | Asp | Phe | Tyr | His | Phe | Lys | Cys | Val |
| | | | 195 | | | | | 200 | | | | | 205 | | |
| Ser | Ser | Lys | Thr | Lys | Gln | Thr | Ser | Lys | Asn | Thr | Leu | Lys | Thr | Val | Met |
| | | 210 | | | | | 215 | | | | | 220 | | | |
| Arg | Ala | Phe | Ile | Ile | Leu | Tyr | Ala | Leu | Arg | Lys | Thr | Phe | Ile | Met | Val |
| 225 | | | | | 230 | | | | | 235 | | | | | 240 |
| Phe | Lys | Ile | Leu | Gly | His | Leu | His | Leu | Gln | Leu | Thr | Arg | Ser | Thr | Met |
| | | | | 245 | | | | | 250 | | | | | 255 | |
| Gln | Leu | Lys | Lys | Gln | Pro | Asn | Tyr | Phe | Leu | Leu | Lys | Thr | Arg | Cys | Phe |
| | | | 260 | | | | | 265 | | | | | 270 | | |
| Leu | His | Glu | Lys | Ile | Leu | Tyr | Val | Cys | Leu | Arg | Cys | Gln | Phe | Tyr | Lys |
| | | | 275 | | | | | 280 | | | | | 285 | | |
| Ser | Val | Phe | Arg | Phe | His | Pro | Leu | Leu | Ala | His | Phe | Ile | Ile | Cys | Ile |
| | | 290 | | | | | 295 | | | | | 300 | | | |
| Phe | Phe | Leu | Tyr | Arg | Thr | Lys | Tyr | Ile | Leu | Phe | Thr | Cys | Met | Ser | Thr |
| 305 | | | | | 310 | | | | | 315 | | | | | 320 |
| His | Tyr | Phe | Phe | Pro | Val | Ser | Ile | Glu | Asn | Pro | Asn | Arg | Leu | Ile | Ile |
| | | | | 325 | | | | | 330 | | | | | 335 | |
| Gly | | | | | | | | | | | | | | | |

IRON TRANSPORT PROTEIN

This application is a continuation of provisional application No. 60/019,528, filed Jun. 6, 1996 now abandoned, and a continuation of provisional application No. 60/056,915, filed Feb. 26, 1996 now abandoned.

This invention was supported by NIH Grant Nos. DK45737 and DK07703, and the government has certain rights to the invention.

FIELD OF THE INVENTION

This invention is in the field of cellular physiology, and in particular, relates to iron transport in cells. The novel protein and compositions of the invention are useful in modulating iron uptake in cells.

BACKGROUND OF THE INVENTION

Ionic iron is an essential metal for the growth and maintenance of animals and most microorganisms. In humans, iron is required for oxygen metabolism, hemoglobin production, and electron transfer reactions, among many other reactions. Ionic iron is actively transported in to the mucosal cells of the intestine, where it binds to the protein ferritin. This phenomenon is called the mucosal iron barrier. The iron-ferritin complex then serves as a local intracellular storehouse for iron. When body reserves of iron are adequate, very little iron is allowed to pass into the portal blood, and most of the stored iron is lost as the epithelial cells later slough off. As iron reserves are depleted, as occurs during acute or chronic hemorrhage, iron uptake from the intestine and its release to the blood are accelerated.

In blood, iron binds to transferrin, a plasma protein that transports it to cells. Transferrin bound iron is delivered to cells, by binding to transferrin cell surface receptors and is endocytosed into acidic intracellular compartments. The low pH of intracellular endosomal domains promotes the release of iron from transferrin while bound to its receptor. Recent studies indicate, however, that there is an alternative pathway for cellular iron transport, which is independent of the transferrin mediated pathway. In this pathway, non-transferrin bound iron uptake does not appear to be influenced by intracellular iron levels. Inman and Wessling-Resnick, *J. Biol. Chem.*, 268:8521–8528 (1993).

Iron deficiencies can cause iron deficient anemia in a patient. Iron deficiency also results in gastrointestinal problems, anorexia, and paresthesia. Anemia is usually treated with a combination therapy of diet, iron supplements, and additional vitamins, such as vitamin B-12 and folic acid to increase the absorption of iron. Pregnant women in particular are most often provided with iron supplements to guard against iron-deficiency.

There are several disorders that are the result of iron overload, including damage to the liver (cirrhosis), the heart, and the pancreas. Hemochromatosis, a genetic disorder with approximately one in twenty people carrying the mutant gene for genetic hemochromatosis, results in excess iron being deposited in the tissues and in increased incidence of hepatic cancer and liver cirrhosis, although clinical symptoms of patients homozygous for this disease may vary. Another hereditary disease characterized by chronic iron overload is Cooley's anemia (Thallasemia major), where congestive heart failure often precedes rapid deterioration and death of the untreated patient almost always in early infancy. In addition, repeated blood transfusions may cause transfusional siderosis, the accumulation of excess iron in the body. The iron liberated from the transfused cells cannot be excreted and accumulates in the cells of the reticuloendothelial system and in cardiac muscle, kidneys, thyroid gland and adrenal gland. Changes in iron distribution from the primary reticuloendothelial iron to parenchymal iron overload are ascribed to the high saturation of transferrin, which provides favorable conditions for uptake of iron by parenchymal cells. Free transferrin thus protects the tissues from siderosis.

Iron (III) chelators are used in the treatment of iron overload and of infectious diseases caused by iron-dependent pathogens. Iron chelator compounds work by forming a stable complex that prevents the iron from entering into further chemical reactions. Different iron chelators have different modes of action. Deferoxamine mesylate chelates iron from ferritin and hemosiderin, but not readily from transferring it does not combine with the iron from cytochromes and hemoglobin. A disadvantage of deferoxamine mesylate is that it can render the patient more susceptible to infections from bacteria and fungi, which can obtain iron directly from their environment or by secretion of low molecular weight siderophores that bind iron (III) at high affinity and return to the cell surface where iron delivery occurs via receptor mediated uptake.

It is a continuing goal of researchers to develop pharmaceutics which can regulate the levels of cellular iron and thus treat iron deficient conditions and iron overload disorders and diseases.

SUMMARY OF THE INVENTION

This invention is directed to a novel protein of general significance to the cellular transport of nontransferrin bound iron. This heretofore unidentified protein, which is termed "stimulator of Fe (iron) transport" (SFT) protein, is essential to an alternative pathway of iron uptake. The cDNA encoding the SFT protein has been cloned and sequenced. The gene for the SFT protein has been mapped to chromosome 10, 17% of the distance from the centromere to the telomere of chromosome arm 10q, an area that corresponds to band 10q21. In addition, the amino acid structural identity of the SFT protein has been deduced, represented in a predicted transmembrane structure with a 6-transmembrane motif.

In one aspect, then, the invention is directed to purified and isolated peptide domains comprising the SFT protein and to molecules that mimic its structure and/or function, which may be used for inducing or modulating iron uptake. Chemical compounds that disrupt the function of the SFT protein have utility as iron uptake modulating agents. Accordingly, in another aspect, the invention is direct to agents capable of disrupting SFT protein function. These agents include, but are not limited to, molecules that bind to the SFT protein, molecules that interfere with the interaction of the SFT protein with other protein(s), and molecules comprising the SFT protein which is altered in some manner. The invention provides methods to identify molecules that modulate iron uptake by disrupting the function of the SFT protein, which accordingly comprise additional contemplated embodiments.

In additional aspects, the present invention relates to products and processes involved in the cloning, preparation and expression of peptide domains comprising the SFT protein; antibodies with specificity to the SFT protein; and nucleotide sequences encoding the SFT protein or portions thereof. Peptide domains comprising the SFT protein are useful for producing antibodies thereto. These antibodies are useful for detecting and isolating proteins comprising the SFT protein in biological specimens, including for example, cells from all human tissue, especially the liver, the spleen, the intestines, and bone marrow.

In yet another aspect, the invention provides for expression vectors containing genetic sequences, hosts transformed with such expression vectors, and methods for producing the recombinant SFT protein of the invention.

The invention relates to the therapeutic use of peptides comprising the SFT protein.

The invention also relates to methods for modulating the iron uptake of a patient by administering peptides comprising the SFT protein, or analogues thereof, to a patient suffering from deficient iron uptake in order to restore normal iron uptake.

The structural information of the SFT protein may be used to develop interventions against iron deficient anemias and iron overload. Thus, pharmaceuticals may be devised based on the SFT structure to either stimulate or block iron uptake.

These and other objects and aspects of the invention will be apparent to those of skill from the description which follows.

BRIEF DESCRIPTION OF THE DRAWINGS

FIG. 1 is the nucleotide sequence of the SFT protein. SEQ ID NO. 1.

FIG. 2 is the amino acid sequence of the SFT protein. SEQ ID NO. 2.

DETAILED DESCRIPTION OF THE INVENTION

Technical and scientific terms used herein have the meanings commonly understood by one of ordinary skill in the art to which the present invention pertains, unless otherwise defined. Reference is made herein to various methodologies known to those of skill in the art publications and other materials setting forth such known methodologies to which reference is made are incorporated herein by reference in their entireties as though set forth in full. Standard reference works setting forth the general principles of recombinant DNA technology include Sambrook, J., et al., *Molecular Cloning: A Laboratory Manual* 2d Ed., Cold Spring Harbor Laboratory press, Planview, N.Y. (1989); Mcpherson, M. J., Ed., *Directed Mutagenesis: A practical Approach*, IRL press, Oxford (1991); Jones, J., *Amino Acid and peptide Synthesis*, Oxford Science publications, Oxford (1992); Austen, B. M. and Westwood, O. M. R., *Protein Targeting and Secretion*, IRL press, Oxford (1991). Any suitable materials and/or methods known to those of skill can be utilized in carrying out the present invention; however, preferred materials and/or methods are described. Materials, reagents and the like to which reference is made in the following description and examples are obtainable from commercial sources, unless otherwise noted.

A previously unidentified protein that appears to be both necessary and sufficient for nontransferrin bound iron uptake has now been identified. This protein, designated herein as the "SFT protein," (stimulator of Fe (iron) transport) mediates iron uptake function. As those of skill familiar with the present invention will appreciate, peptide domains comprising the SFT protein are useful in modulating iron uptake in cells. Similarly, compounds and compositions which are capable of binding to the SFT protein are useful as agents for the modulation of iron uptake activity in cells.

As used herein, the term "SFT protein " refers to a protein domain first identified in a human erythroleukemia cell line (K562), demonstrated herein to be essential for iron uptake; and to peptide domains and/or molecules capable of mimicking its structure and/or function. In a preferred embodiment, the present invention comprises a protein having the amino acid sequence identified in SEQ ID NO. 2, as well as functional equivalents thereof. By "functional equivalent" is meant a peptide domain possessing a biological activity or immunological characteristic substantially similar to that of the SFT protein, and is intended to include "fragments", "variants", "analogs", "homologs", or "chemical derivatives" possessing such activity or characteristic. Functional equivalents of the SFT domains, then, may not share an identical amino acid sequence, and conservative or non-conservative amino acid substitutions of conventional or unconventional amino acids are possible.

Reference herein to "conservative" amino acid substitution is intended to mean the interchangeability of amino acid residues having similar side chains. For example, glycine, alanine, valine, leucine and isoleucine make up a group of amino acids having aliphatic side chains; serine and threonine are amino acids having aliphatic-hydroxyl side chains; asparagine and glutamine are amino acids having amide-containing side chains; phenylalanine, tyrosine and tryptophan are amino acids having aromatic side chains; lysine, arginine and histidine are amino acids having basic side chains; and cysteine and methionine are amino acids having sulfur-containing side chains. Interchanging one amino acid from a given group with another amino acid from that same group would be considered a conservative substitution. Preferred conservative substitution groups include asparagine-glutamine, alanine-valine, lysine-arginine, phenylalanine-tyrosine and valine-leucine-isoleucine.

Agents capable of modulating iron transport or iron uptake mediated by the SFT protein may include peptide domains comprising the SFT protein, as well as mutants of the SFT protein. A "mutant" as used herein refers to a peptide having an amino acid sequence which differs from that of the naturally occurring peptide or protein by at least one amino acid. Mutants may have the same biological and immunological activity as the naturally occurring SFT protein. However, the biological or immunological activity of mutants may differ or be lacking. For example, a SFT protein mutant may lack the biological activity which characterizes naturally occurring SFT protein, but may be useful as an antigen for raising antibodies against the SFT protein or for the detection or purification of antibodies against the SFT protein, or as an agonist (competitive or non-competitive), antagonist, or partial agonist of the function of the naturally occurring SFT protein.

Modulation of iron uptake or iron transport mediated by the SFT protein may be effected by agonists or antagonists of SFT protein as well. Screening of peptide libraries, compound libraries and other information gene banks to identify agonists or antagonists of the function of proteins comprising the SFT protein is accomplished with assays for detecting the ability of potential agonists or antagonists to inhibit or augment SFT iron transport.

For example, high through-put screening assays may be used to identify compounds that modulate the iron transport function of the SFT protein. These screening assays facilitate the identification of compounds that accelerate or inhibit iron transport by influencing iron transport mediated by the SFT protein. For example, an in vitro screen for compounds that disrupt the SFT protein interaction with iron comprises multiwell plates coated with SFT protein which are incubated with a labeled iron in the presence of one or more compounds to be tested. Molecules that specifically disrupt the interaction could, in principle, bind to either the SFT protein "ligand" or interfere with the labelled iron. Either class of compound would be a candidate iron modulating agent.

A high speed screen for agents that bind directly to the SFT protein may employ immobilized or "tagged" combinatorial libraries. Agents that bind specifically to such libraries are candidates to be tested for their capacity to block iron uptake activity. As discussed above, such agents may function as suppressors of iron uptake by directly inhibiting SFT protein function. These agents would be useful for suppressing aberrant iron uptake in iron overload disorders and diseases.

Antibodies against the SFT protein of the invention may be used to screen cDNA expression libraries for identifying clones containing cDNA inserts encoding structurally related, immunocrossreactive proteins which may be members of the family of SFT protein. Screening of cDNA and mRNA expression libraries is known in the art. Similarly, antibodies against the SFT protein are used to identify or purify immunocrossreactive proteins related to this peptide, or to detect or determine the amount of proteins containing the SFT protein in a cell or cell population, for example, in tissue or cells, such as hepatocytes. Known methods for such measurements include immunoprecipitation of cell extracts followed by PAGE, in situ detection by immunohistochemical methods, and ELISA methods, all of which are well known in the art.

Modulation of iron uptake according to the invention includes methods employing specific antisense polynucleotides complimentary to all or part of the nucleotide sequences encoding peptide domains comprising the SFT protein or antisense polynucleotides complimentary to all or part of the 3' or 5' noncoding regions of the SFT protein. Such complimentary antisense polynucleotides may include nucleotide additions, deletions, substitutions and transpositions, providing that specific hybridization to the target sequence persists. Soluble antisense RNA or DNA oligonucleotides which can hybridize specifically to mRNA species encoding proteins comprising the SFT protein, and which prevent transcription of the mRNA species and/or translation of the encoded polypeptide are contemplated as complimentary antisense polynucleotides according to the invention. Production of peptide domains comprising the SFT protein is inhibited by antisense polynucleotides according to the invention, and such antisense polynucleotides may inhibit iron uptake, and/or reverse the transformed phenotype of cells. In addition, riboregulators which effectively prohibit the transcription or translation of a protein may also be employed as an antisense polynucleotide. A heterologous expression cassette maybe used to produce antisense polynucleotides in a transfectant or transgenic cell. Antisense polynudeotides also may be administered as soluble oligonucleotides to the external environment of the target cell, such as the culture medium of cells in vitro or the interstitial fluid (e.g., via the circulatory system) in vivo. Antisense polynucleotides and their use are known to those of skill, and are described, for example, in Melton, D. A., Ed. *Antisense RNA and DNA*, Cold Spring Harbor Laboratory press, Cold Spring Harbor, N.Y. (1988).

Computer-aided molecular modeling of the SFT protein can be used to study its three-dimensional structures using computer visualization techniques. Novel designs of low molecular weight inhibitors or oligopeptides can then be analyzed for selective inhibition. Descriptions of targeted drug design can be found in I. Kuntz, "Structure-Based Strategies for Drug Design and Discovery," *Science*, 257:1078–1082 (1992) and J. Dixon, "Computer-Aided Drug Design: Getting the Best Results," *Trends in Biotechnology* 10:357–363 (1992). Specific applications of the binding of inhibitors to targets using computer modeling have been described in piper et al., "Studies Aided by Molecular Graphics of Effects of Structural Modifications on the Binding of Antifolate Inhibitors to Human Dihydrofolate Reductase," *Proc Am. Assoc. Cancer Res. Annual Meeting*, 33:412 (1992); Hibert et al., "Receptor 3D-Models and Drug Design," *Therapie* (Paris), 46:445–451 (1991) (serotonin receptor recognition sites). Computer programs that can be used to conduct three-dimensional molecular modeling are described in G. Klopman, "Multicase 1: A Hierarchical Computer Automated Structure Evaluation Program," *Quantitative Structure-Activity Relationships*, 11:176–184 (1992); pastor et al., "The Edisdar programs Rational Drug Series Design," *Quantitative Structure-Activity Relationships*, 10:350–358 (1991); Bolis et al., "A Machine Learning Approach to Computer-Aided Molecular Design," *J. Computer Aided Molecular Design*, 5:617–628 (1991); and Lawrence and Davis, "CLIX: A Search Algorithm for Finding Novel Ligands Capable of Binding proteins of Known Three-Dimensional Structure," *Proteins Structure Functional Genetics* 12:31–41 (1992).

Low molecular weight inhibitors specific for the SFT protein can be predicted by molecular modeling and synthesized by standard organic chemistry techniques. Computer modeling can identify oligopeptides which block the iron transport activity. Techniques for producing the identified oligopeptides are well known and can proceed by organic synthesis of amino acids, by genetic engineering techniques, or by PCR based amplification. R. Silverman, *The Organic Chemistry of Drug Design and Drug Action*, Academic Press (1992).

The inhibitors of this invention can be identified by selecting those inhibitors that selectively inhibit the iron transport ability of the SFT protein.

Peptidomimetics of the SFT protein are also provided by the present invention, and can act as drugs for the modulation of iron uptake by, for example, blocking or interfering with the function of peptide domains comprising the SFT protein. peptidomimetics are commonly understood in the pharmaceutical industry to include non-peptide drugs having properties analogous to those of those of the mimicked peptide. The principles and practices of peptidomimetic design are known in the art and are described, for example, in Fauchere J., *Adv. Drug Res.* 15:29 (1986); and Evans et al., *J. Med. Chem.* 30:1229 (1987). Peptidomimetics which bear structural similarity to therapeutically useful peptides may be used to produce an equivalent therapeutic or prophylactic effect. Typically, such peptidomimetics have one or more peptide linkages optionally replaced by a linkage which may convert desirable properties such as resistance to chemical breakdown in vivo. These linkages may include $—CH_2NH—$, $—CH_2S—$, $—CH_2—CH_2—$, $—CH{=}CH—$, $—COCH_2—$, $—CH(OH)CH_2—$, and $—CH_2SO—$. Peptidomimetics may exhibit enhanced pharmacological properties (biological half life, absorption rates, etc.), different specificity, increased stability, production economies, lessened antigenicity and the like which makes their use as therapeutics particularly desirable.

It is possible, then, to employ the invention for detection or determination of peptide domains comprising the SF1 protein, for example, in fractions from tissue/organ excisions, by means of immunochemical or other techniques in view of the antigenic properties thereof. Immunization of animals with peptide domains comprising the SFT protein alone or in conjunction with adjuvants by known methods can produce antibodies specific for the SFT protein. Antiserum obtained by conventional procedures may be utilized for this purpose. For example, a mammal, such as a rabbit, may be immunized with a peptide domain comprising the SFT protein, thereby inducing the formation of polyclonal antibodies thereagainst. Monoclonal antibodies also may be generated using known procedures. Such antibodies can be used according to the invention to detect the presence and amount of peptide domains comprising the SFT protein.

The SFT protein and other compositions of the present invention may be produced by recombinant DNA techniques known in the art. For example, nucleotide sequences encoding the SFT protein of the invention may be inserted into a suitable DNA vector, such as a plasmid, and the vector used to transform a suitable host. The recombinant SFT protein is produced in the host by expression. The transformed host may be a prokaryotic or eukaryotic cell. Preferred nucleotide sequences for this purpose encoding the SFT protein is set forth in SEQ ID NO. 1.

polynucleotides encoding peptides comprising the SFT protein may be genomic or cDNA, isolated from clone libraries by conventional methods including hybridization screening methods. Alternatively, synthetic polynucleotide sequences may be constructed by known chemical synthetic methods for the synthesis of oligonucleotides. These synthetic methods are described, for example, in Blackburn, G. M. and Gait, M. J., Ed., *Nucleic Acids in Chemistry and Biology*, IRL press, Oxford, England (1990), and it will be evident that commercially available oligonucleotide synthesizers also may be used according to the manufacturer's instructions.

polymerase chain reaction (PCR) using primers based on the nucleotide sequence data disclosed herein may be used to amplify DNA fragments from mRNA pools, cDNA clone libraries or genomic DNA. PCR nucleotide amplification methods are known in the art and are described, for example, in Erlich, H. A., Ed., *PCR Technology: Principles and Applications for DNA Amplification*, Stockton press, New York, N.Y. (1989); U.S. Pat. No. 4,683,202; U.S. Pat. No. 4,800,159; and U.S. Pat. No. 4,683,195. Various nucleotide deletions, additions and substitutions may be incorporated into the polynucleotides of the invention as will be recognized by those of skill, who will also recognize that variation in the nucleotide sequence encoding SFT protein may occur as a result of, for example, allelic polymorphisms, minor sequencing errors, and the like. The polynucleotides encoding SFT protein of the invention may include short oligonucleotides which are useful, for example, as hybridization probes and PCR primers. The polynucleotide sequences of the invention also may comprise a portion of a larger polynucleotide and, through polynucleotide linkage, they may be fused, in frame, with one or more polynucleotide sequences encoding different proteins. In this event, the expressed protein may comprise a fusion protein. Of course, the polynucleotide sequences of the invention may be used in the PCR method to detect the presence of mRNA encoding SFT protein in the diagnosis of disease or in forensic analysis.

cDNAs encoding proteins which interact with the SFT protein (or proteins containing the SFT protein) can be identified by screening cDNA expression libraries, employing known methods. Examples of such methods include the yeast two-hybrid system (Chien, et al., proc. Nat'l. Acad. Sci. 88: 9578 (1991), and the *E. coli*/BCCp interactive screening system (Germino, et al., proc. Nat'l. Acad. Sci. 90: 1639 (1993). Suitable cDNA libraries will include mammalian cDNA libraries, such as human, mouse or rat, which may contain cDNA produced from RNA and a single cell, tissue or organ type or developmental stage, as are known in the art.

A nucleotide sequence encoding the SFT protein or a peptide domain thereof may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, for example, by Sambrook, et al., (In: *Molecular Cloning, A Laboratory Manual*, Cold Spring Harbor Laboratories, Cold Spring Harbor, N.Y. Second Edition (1989)), and are well known in the art.

The rational design of SFT protein mimetics or binding molecules, based on modeled (or experimentally determined) peptide structure, may be carried out by those of skill, using known methods of rational drug design. Therapeutic or prophylactic methods for treating iron overload and the like, are accomplished by the administration of an effective amount of a therapeutic agent capable of specifically inhibiting SFT protein, thereby modulating the iron transport activity of the SFT protein.

Any mode of administration which results in the delivery of the therapeutic agent across the cell membrane and into the desired cell is contemplated as within the scope of the present invention. The site of administration and cells will be selected by one of ordinary skill in the art based upon an understanding of the particular degenerative disorder being treated. In addition, the dosage amount, dosage frequency, and length of course of treatment, can be determined and optimized by one of ordinary skill in the art depending upon the particular disorder being treated. The particular mode of administration can also be readily selected by one of ordinary skill in the art and can include, for example, oral, intravenous, subcutaneous, intramuscular, etc., with the requirement that the therapeutic agent cross the cell membrane. Principles of pharmaceutical dosage and drug delivery are known and are described, for example, in Ansel, H. C. and Popovich, N. G., *Pharmaceutical Dosage Forms and Drug Delivery Systems*, 5th Edition, Lea & Febiger, Publisher, Philadelphia, Pa. (1990). It is possible, for example, to utilize liposomes to specifically deliver the agents of the invention. Liposomes can be produced so that they contain additional bioactive compounds and the like, such as drugs, radioisotopes, lectins and toxins, which would act at the target site.

Suitable agents for use according to the invention include SFT protein and mimetics, peptide domains, fragments, functional equivalents and/or hybrids or mutants thereof, as well as vectors containing cDNA encoding any of the foregoing. Agents can be administered alone or in combination with and/or concurrently with other suitable drugs and/or courses of therapy.

In addition, cells and non-human transgenic animals having one or more functionally impaired alleles encoding the SFT protein or peptide domain may be generated using homologous targeting constructs from genomic clones. Methods for the production of homologous targeting constructs are known and described, for example, in Bradley, et al., *Bio/Technology* 10:534 (1992); and Koh, et al., *Science* 256: 1210 (1992). For example, "knock-out" mice may be generated which are homozygous or heterozygous for an inactivated allele of a protein comprising the SFI protein by use of homologous targeting. These mice are useful as research subjects for the investigation of disease and for other uses. Methods of producing chimeric targeted mice are known and are described, for example, in Robertson, E. J., Ed., *Teratocarcinomas and Embryonic Stem Cells: A practical Approach*, IRL Press, Washington, D.C. (1987), which also describes the manipulation of embryonic stem cells. In addition, transgenes for expressing polypeptides comprising the SFT protein at high levels or under the control of selected transcription control sequences may be constructed using the cDNA or genomic gene of a protein comprising the SFF protein. Transgenes so constructed can be introduced into cells and transgenic non-human animals by known methods. Such transgenic cells and transgenic non-human animals may be used as screens for agents which modulate iron uptake.

The examples below are provided to illustrate the subject invention. These examples are provided by way of illustration and are not included for the purpose of limiting the invention in any way.

EXAMPLES

The present inventors have derived from molecular cloning of the human stimulator of Fe (iron) transport (SFT) cDNA the complete primary structure of human SFT. SFT is ubiquitously expressed indicating that the activity of this protein is most likely an essential element of iron transport in all tissues. Since iron is a required essential nutrient for cell survival and growth, SFT appears to play a key role in iron metabolism and is likely to be regulated in states of iron-deficient anemia and iron overload (hemochromatosis).

Isolation of RNA and Synthesis of First Strand cDNA: Total RNA was isolated from human K562 erythroleukemia cells stimulated by phorbol esters to enhance iron uptake (Akompong et al., J. Biol. Chem., 270: 20937–20941 (1995)) using the guanidinium isothiocyanate method (Chirgwin et al., Biochemistry, 18: 5294–5299), polyadenylated RNA was isolated using the Invitrogen "FastTrack" System (Invitrogen, San Diego, Calif.). First-strand cDNA synthesis from the human K562 cell polyadenylated RNA was accomplished using an oligo-dT$_{17}$ primer containing a NotI restriction at the 5' end (Promega, Madison, Wis.) using procedure described by Gubler and Hofman, Gene, 25: 263.

Functional Expression Cloning of SFT cDNA: Human K562 cell cDNA was directionally subcloned into pBluecript SK(-) (Stratagene, La Jolla, Calif.). Briefly, EcoRI linkers were ligated to the 5' ends of the cDNA which was subsequently digested with NotI. This K562 cell cDNA library was transformed into XLIBlue cells (Stratagene, La Jolla, Calif.). Approximately forty-thousand independent colonies of these cells were separated into 5 pools for plasmid isolation. The plasmid cDNAs were then subject to in vitro transcription and capping using the "mCap" kit (Stratagene, La Jolla, Calif.). Transcripts (~20 to 25 ng) prepared from these pools were then injected both individually in combination into oocytes isolated from *Xenopus laevis*. After a 48 hour incubation at 20° C. to permit expression of proteins from the injected cRNAs, oocytes were subsequently assayed for the ability to take up radioactive iron using methods adapted from Inman and Wessling-Resnick, J. Biol. Chem. 268: 8521–8528 (1993). XLIBlue cells identified to carry plasmid which directed transcription of the apparent iron transport activity were further subdivided into a second set of 5 pools for plasmid isolation and preparation of cRNAs to inject into Xenopus oocytes for iron transport assays. Iterative screening in this manner led to the isolation of a single 1403 base pair clone with which iron transport activity could be expressed when co-injected with a second pool of four independent clones. Sequencing of both strands of the 1403 base pair clone was performed with flanking and internal primers by the dideoxy chain-termination method of Sanger et al., proc. Nat'l. Acad. Sci. USA, 74: 5463–5467.

Sequence data was analyzed using programs available through the National Institutes of Health sponsored Molecular Biology Computer Research Resource of the Dana Farber Cancer Institute/Harvard School of public Health. A search using the BLAST algorithm (Altschul et al. J. Mol. Biol., 215: 403) of all available data bases (including non-redundant PDB, GBupdate, GenBank, EMBLupdate, and EMBL) revealed that this clone was a heretofore unidentified species. A single open reading frame predicted to encode a 338 amino acid protein was identified and further subcloned into the transcription-computer vector pAGA (Sanford et al., J. Biol. Chem., 266: 9570–9579). Following in vitro transcription and capping, cRNAs containing the open reading frame were injected into Xenopus oocytes. Iron transport assays demonstrated that injection of this transcript alone (absent of 5' and 3' regions of the original full-length clone) was sufficient to confer iron uptake activity to the oocytes, thus confirming-that the identified coding sequence dictated synthesis for SFT itself.

Northern Analysis: A commercially available multiple tissue Northern blot containing various human tissues (Clontech, Palo Alto, Calif.) was used for analysis of SFT expression with methods described by the manufacturer. As a probe, the 1403 bp fragment of the SFT gene was labelled with [32P]-dCTP by random priming (Pharmacia Oligolabelling Kit, Pharmacia, Piscataway, N.J.). Two mRNAS of ~2.4 and ~1.5 kilobases were hybridized by the SFT probe and were present in all tissues examined including spleen, thymus, intestine, and peripheral blood leukocytes.

Miscellaneous: All molecular biology protocols employed, including restriction enzyme digests, ligation reactions, DNA sequencing, plasmid isolation, etc., were standard techniques described, for example, in Sambrook, J. et al., *Molecular Cloning: A Laboratory Manual*, 2nd ed., Cold Spring Harbor Laboratory Press, Planview, N. Y. (1989).

Deposit Information: A culture containing the SFT cDNA was deposited with the American Type Culture Collection (ATCC) at 12301 Parklawn Drive, Rockville, Md. 20852 USA on Mar. 20, 1996.

Although the foregoing invention has been described in some detail by way of illustration and example for purposes of clarity and understanding, it will be obvious to one skilled in the art that certain changes and modifications may be practiced within the scope of the appended claims.

What is claimed is:

1. An isolated nucleotide sequence encoding the stimulator of Fe (iron) transport (SFT) protein.

2. A method of producing the stimulator of Fe (iron) (SFT) transport protein comprising the steps of:
   a. inserting the nucleotide sequence of claim 1 into an expression vector;
   b. transforming in vitro host cells with the vector;
   c. expressing the protein in the host cells; and
   d. isolating the protein.

3. An expression vector comprising the nucleotide sequence of claim 1.

4. An in vitro host cell transformed by the expression vector of claim 3.

5. An isolated nucleotide consisting of the nucleotide sequence of SEQ ID NO: 1.

6. A method of production the stimulator of Fe (iron) (SFT) transport protein comprising the steps of:
   a. inserting the nucleotide sequence of claim 5 into an expression vector;
   b. transforming in vitro host cells with the vector;
   c. expressing the protein in the host cells; and
   d. isolating the protein.

7. An expression vector comprising the nucleotide sequence of claim 5.

8. An in vitro host cell transformed by the expression vector of claim 7.

9. The host cell of claims 4 or 8 wherein the cell is a prokaryotic or eukaryotic cell.

* * * * *